United States Patent
Romano

(10) Patent No.: US 10,271,742 B2
(45) Date of Patent: Apr. 30, 2019

(54) AUTOMATIC METHOD FOR MEASURING AND PROCESSING BLOOD PRESSURE

(71) Applicant: Salvatore Romano, Florence (IT)

(72) Inventor: Salvatore Romano, Florence (IT)

(*) Notice: Subject to any disclaimer, the term of this patent is extended or adjusted under 35 U.S.C. 154(b) by 0 days.

(21) Appl. No.: 15/365,804

(22) Filed: Nov. 30, 2016

(65) Prior Publication Data

US 2017/0086685 A1 Mar. 30, 2017

Related U.S. Application Data

(63) Continuation of application No. 13/818,985, filed as application No. PCT/IT2011/000308 on Sep. 5, 2011, now abandoned.

(30) Foreign Application Priority Data

Sep. 6, 2010 (IT) .............................. RM2010A0468

(51) Int. Cl.
| | |
|---|---|
| *A61B 5/02* | (2006.01) |
| *A61B 5/021* | (2006.01) |
| *A61B 5/0215* | (2006.01) |
| *A61B 5/00* | (2006.01) |

(52) U.S. Cl.
CPC ........ *A61B 5/02125* (2013.01); *A61B 5/0215* (2013.01); *A61B 5/02108* (2013.01); *A61B 5/725* (2013.01); *A61B 5/7239* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 5,743,267 A | 4/1998 | Nikolic et al. | |
| 6,758,822 B2 | 7/2004 | Romano | |
| 7,468,035 B2 | 12/2008 | Bonan et al. | |
| 2004/0097813 A1 | 5/2004 | Williams | |
| 2006/0064021 A1* | 3/2006 | Hefele ................. | A61B 5/0215 600/486 |
| 2013/0172761 A1 | 7/2013 | Romano | |

OTHER PUBLICATIONS

International Search Report issued in parent PCT Application No. PCT/IT2011/000308 dated Jan. 12, 2012.
International Preliminary Examination Report issued in parent PCT Application No. PCT/IT2011/000308 dated Mar. 12, 2013.
U.S. Appl. No. 13/820,853, filed Mar. 5, 2013.
Office Action issued in the U.S. Appl. No. 13/820,853 (US Publication No. 2013/0172761 A1) dated Nov. 2, 2015.

* cited by examiner

*Primary Examiner* — Christian Jang
*Assistant Examiner* — Karen Toth
(74) *Attorney, Agent, or Firm* — Hershkovitz & Associates, PLLC; Abe Hershkovitz

(57) ABSTRACT

Automatic method, as well as the related system and the tools allowing the same to be executed, for measuring and processing blood pressure starting from a detected pressure signal, the method operating in the time domain for discriminating whether the detected signal is an adequate measurement or not and, where it is not, time domain analysis automatically selects a low-pass filter to, possibly iteratively, apply to the detected pressure signal for having correct values and wave form of the blood pressure.

18 Claims, 4 Drawing Sheets

AUTOMATIC METHOD FOR MEASURING AND PROCESSING BLOOD PRESSURE

CROSS-REFERENCE TO RELATED APPLICATIONS

This Application is a Continuation of application Ser. No. 13/818,985 filed Feb. 25, 2013, pending, which is a US § 371 National Stage based on PCT/IT2011/000308 filed Sep. 5, 2011 and published as WO 2012/032553 A1 on Mar. 15, 2012, which claims priority of Italian Application No. RM2010A000468 filed Sep. 6, 2010, the disclosures of which are incorporated in their entirety herein by reference.

SUMMARY OF THE INVENTION

The present invention relates to an automatic method for measuring and processing blood pressure that allows in a reliable, versatile, effective, simple, and inexpensive way, to correctly measure blood pressure, dynamically adapting to variability of the latter, eliminating the artefacts introduced by the conventional systems.

The present invention further relates to the related detecting apparatus, as well as to the tools allowing the method to be executed.

It is known that measurement of the blood pressure, also called arterial pressure, may occur either invasively or non-invasively.

The invasive measurement is generally performed through a filling pressure line, connected to an invasive catheter, provided at the end with a transduction system transforming detected pressure into a potential difference. Differently from the non-invasive measuring systems, such as for instance the Riva-Rocci cuff, the invasive measurement emphasises not only the maximum and the minimum of the measured pressure, but also the morphology of detected signal.

Consequently, the invasive measurement, besides being more reliable than the non-invasive measurement, is capable to emphasise the characteristics of heart-arterial circle coupling which directly affect the detected result. In fact, the systolic and diastolic pressure values and the whole morphology of the heart beat are strictly related to the contractility of the heart and to the circulatory system, identified in the so-called dynamic impedance $Z_d(t)$, linked to the pressure-volume (P-V) curve and given by the ratio between a pressure value and a time range.

However, evaluation techniques based on the invasive measurement of the blood pressure often suffer from problems of significant inaccuracy in measurements of maximum and minimum pressure and, consequently, also in its morphology. In fact, many authors have shown the existence of an inadequate underdamping of the pressure signal that may lead to considerable measurement errors, also of several tens of mmHg.

In order to solve such problems, some solutions have been proposed which are based on the application of low-pass filters to the pressure signal (i.e. on a frequency processing of the pressure signal that imposes from outside a fixed value of the cutoff frequency) and/or on the use of mechanical systems capable to damp the frequency components of the detected pressure wave.

In particular, the mechanical systems currently used for determining whether the detected signal has a correct underdamping or not employ the mechanical method of the square wave test described by R. M. Gardner in "Direct Blood Pressure Measurement—Dynamic Response Requirements", Anesthesiology, March 1981, Volume 54, Issue 3, ppg 227-236, that requires a visual observation of the detected pressure signal by a physician. This is the case, for instance, of the R.O.S.E.™ (Resonance Over Shoot Eliminator, available from the US company Becton Dickinson Critical Care System Ltd.) systems and in the Accudynamic® systems (available from the HOSPIRA—ICU Medical). These systems mechanically act by imposing a mechanical damping: in the Accudynamic® system such mechanical damping is adjustable in a small damping range through a small knob advancing a pin that penetrates in different depths in the pressure line; instead, in the ROSE system, the mechanical damping is fixed by a micro-bubble and elastic membrane device, thus acting in a fixed way for any pressure signal (well defined fixed damping).

However, all these systems operate in a pre-determined (static) manner on a dynamic problem, because only the frequency spectrum of the signal analysed from the pressure line is considered. This implies that characteristic frequency spectra equal in certain conditions of the patient are adequate, while in other physiopathological conditions they are clearly inadequate, generating high over-evaluation of the arterial pressure.

In fact, correctness of underdamping is a dynamic problem associated (besides the specific cardiocirculatory system of the patient under consideration) with the specific heart beat under consideration, that may thus change from beat to beat, whereby the pressure line responses in a different manner depending on the situation in which it is used.

By way of example, FIG. 1 shows a typical blood pressure signal, wherein the beats change both in their morphology and in measurement of the systolic and diastolic pressure (see FIG. 1a), and the different result that a conventional system for measuring the arterial pressure obtains on a specific beat, in particular in the neighbourhood of the systolic pressure, by applying none or three different cutoff frequencies (no filter, 15 Hz, 10 Hz, 6 Hz) (see FIG. 1b). FIG. 2 shows the differences of the systolic pressure values, on two consecutive beats in a same blood pressure signal (see FIGS. 2a and 2b), obtained by applying none or three different cutoff frequencies (no filter, 15 Hz, 10 Hz, 6 Hz). FIG. 3 shows as a conventional measuring system behaves, in particular in the neighbourhood of the systolic pressure, in detecting a beat by applying none or three different cutoff frequencies (no filter, 15 Hz, 6 Hz) (see FIG. 3a) and by applying none or three different cutoff frequencies (no filter, 10 Hz) (see FIG. 3b); in particular, it is evident that the 6 Hz cutoff frequency causes an overdamping (see FIG. 3a), while the filter with 10 Hz cutoff frequency is the most adequate (see FIG. 3b). FIG. 4 shows two blood pressure signals wherein the same filters act in a different manner: in FIG. 4a the filter with 10 Hz cutoff frequency seems almost ineffective, while in FIG. 4b the same filter with 10 Hz cutoff frequency acts in a significant manner; in particular, for the beats shown in FIG. 4 the filter with 6 Hz cutoff frequency is the most adequate.

Moreover, the response of the pressure transducer depends, along with on the characteristics of length, diameter, type of material and liquid filling the pressure line, also on its coupling to the catheter diameter, on the arterial tone, on the pulse frequency and on the rigidity of the vessel of the subject under examination.

In this regard, in the last years great efforts have been made for optimising the characteristics of length, diameter, filling liquid, type of material and catheter, in order to limit the artefacts. In particular, optical fibre pressure lines have been also made which may reduce the artefacts.

However, all the conventional systems does not manage to completely solve the aforementioned problems of wrong measurement of the arterial pressure, and this is very frequent especially in cases where the detection is most necessary, such as for instance for patients who are elderly, very young, septic, tachycardic and extremely instable both in the arterial tone and in pace (e.g. due to atrial fibrillation).

It is therefore an object of the present invention to allow in a reliable, versatile, effective, simple, and inexpensive way, to correctly measure blood pressure, dynamically adapting to variability of the latter, eliminating the artefacts introduced by the conventional systems.

It is specific subject matter of this invention an automatic method for measuring and processing blood pressure comprising the following steps:

A. having a sampled detected pressure signal P(t) for one or more heart beats, each heart beat starting at an initial instant coinciding with the one of the initial diastolic pressure point and ending at a final instant coinciding with the one of the subsequent diastolic pressure point and comprising a dicrotic point, each beat having a systolic phase going from the initial diastolic point to the dicrotic point; and B. automatically analysing and discriminating morphology of the pressure signal P(t) sampled for each heart beat, determining instant and pressure value of one or more characteristic points of the pressure signal P(t) selected from the group comprising
an initial diastolic pressure point,
a systolic pressure point,
a dicrotic point, and
one or more resonance points, each one of which occurs in an instant wherein a second derivative $d^2P/dt^2$ of the pressure signal P(t) has a local maximum,
at least one characteristic point of the pressure signal P(t) belonging to the systolic phase of the heart beat under consideration and being different from the initial diastolic pressure point;
the method being characterised in that it further comprises the following steps:

C. for each heart beat, determining an energy efficiency RES through the following sub-steps:

C.1 determining a direct dynamic impedance $Z_{d\_D}(t)$ for each one of said one or more characteristic points belonging to the systolic phase of the heart beat under consideration and different from the initial diastolic pressure point, said direct dynamic impedance $Z_{d\_D}(t)$ being equal to the ratio between a value of the pressure signal P(t) at the characteristic point and the distance of the respective time instant from the initial instant of the heart beat under consideration, and determining an impedance $Z_D$ of a direct wave of pressure by summing with alternate signs the values of the direct dynamic impedances $Z_{d\_D}(t)$ ordered according to a direct time order starting from the initial instant of the heart beat under consideration up to the dicrotic point instant, beginning to apply a positive sign to the direct dynamic impedance $Z_{d\_D}(t)$ that is the first one in the direct time order;

C.2 determining a reflected dynamic impedance $Z_{d\_R}(t)$ for each one of said one or more characteristic points, said reflected dynamic impedance $Z_{d\_R}(t)$ being equal to the ratio between a value of the pressure signal P(t) at the characteristic point and the distance of the respective time instant from the final instant of the heart beat under consideration, and determining an impedance $Z_R$ of reflected waves of pressure by summing with alternate signs the values of the reflected dynamic impedances $Z_{d\_R}(t)$ ordered according to a reverse time order starting from the final instant down to the initial instant of the heart beat under consideration, beginning to apply a positive sign to the reflected dynamic impedance $Z_{d\_R}(t)$ that is the first one in the reverse time order;

C.3 determining said energy efficiency RES as ratio between the impedance $Z_D$ of the direct wave and the impedance $Z_R$ of the reflected waves:

$$RES = Z_D/Z_R$$

D. for said energy efficiency RES determined in step C, checking whether a first derivative dP/dt of the pressure signal P(t) is lower than a first value $T_d$ of maximum threshold in the whole heart beat under consideration and whether the second derivative $d^2P/dt^2$ of the pressure signal P(t) is lower than a second value $T_{d2}$ of maximum threshold in the whole heart beat under consideration, and in the case where the check has negative outcome making step E, otherwise, in the case where the check has positive outcome, making step F;

E. selecting a cutoff frequency of a low-pass filter on the basis of said energy efficiency RES determined in step C, of the first derivative dP/dt and of the second derivative $d^2P/dt^2$ of the pressure signal P(t), and applying said low-pass filter to the pressure signal P(t), thus obtaining a new sampled pressure signal, and returning to execute the preceding steps starting from step B;

F. outputting the pressure signal P(t) on which step B has been made for the last time.

Always according to the invention, said one or more resonance points may be determined in step B through the following sub-steps:

B.2 determining a total number $N_{dP\_max}$ of local maximum points of the first derivative dP/dt of the pressure signal P(t) in the heart beat under consideration;

B.3 determining local maximum points of the second derivative $d^2P/dt^2$ of the pressure signal P(t) in the heart beat under consideration; and B.4 selecting a number $N_{dP\_max}$ of local maximum points of the second derivative $d^2P/dt^2$ having largest values, determining $N_{dP\_max}$ time instants $t_{d2P\_max}(i)$ wherein said $N_{dP\_max}$ selected local maximum points of the second derivative $d^2P/dt^2$, occur, and assuming the points of the pressure signal P(t) in such $N_{dP\_max}$ instants $t_{d2P\_max}(i)$ as resonance points.

Still according to the invention, in step B, the following characteristic points of the pressure signal P(t) may be determined:
the initial diastolic pressure point,
the systolic pressure point,
the dicrotic point, and
one or more resonance points.

Furthermore according to the invention, the first value $T_d$ of maximum threshold and the second value $T_{d2}$ of maximum threshold may be functions of said energy efficiency RES determined in step C.

Always according to the invention, in step D, it may be checked whether said energy efficiency RES determined in step C belongs to one of three or more, preferably four, adjacent ranges of variability, the first value $T_d$ of maximum threshold and the second value $T_{d2}$ of maximum threshold being preferably functions of the range to which said energy efficiency RES determined in step C belongs.

Still according to the invention, in step E, said cutoff frequency may be selected by discriminating the belonging of said energy efficiency RES determined in step C to one of three or more, preferably four, adjacent ranges of variability, for each one of said three or more adjacent ranges of variability of said energy efficiency RES determined in step C, discriminating the belonging of the first derivative dP/dt of the pressure signal P(t) in the whole heart beat under consideration to one of three or more, preferably six, adjacent ranges of variability, and for each one of said three or more adjacent ranges of variability of the first derivative dP/dt of the pressure signal P(t) in the whole heart beat under consideration, discriminating the belonging of the second derivative $d^2P/dt^2$ of the pressure signal P(t) to one of three or more, preferably four, non overlapping ranges of variability, to which a respective value of said cutoff frequency corresponds.

Furthermore according to the invention, said cutoff frequency may have a value decreasing upon increasing the first derivative dP/dt of the pressure signal P(t), under identical values of said energy efficiency RES and of the second derivative $d^2P/dt^2$ of the pressure signal P(t).

Always according to the invention, said cutoff frequency may have a value decreasing upon increasing the second derivative $d^2P/dt^2$ of the pressure signal P(t), under identical values of said energy efficiency RES and of the first derivative dP/dt of the pressure signal P(t).

Still according to the invention, said cutoff frequency may range from 0.5 Hz to 100 Hz, preferably from 2 Hz to 80 Hz, more preferably from 3 Hz to 60 Hz.

Furthermore according to the invention, in step F the pressure signal P(t) may be displayed on a display.

It is always specific subject matter of this invention an automatic apparatus for measuring and processing blood pressure characterised in that it comprises processing means capable to perform the steps of the previously described automatic method for measuring and processing blood pressure.

It is still specific subject matter of this invention a computer program, comprising code means adapted to perform, when operating on processing means of an apparatus, the steps of the previously described automatic method for measuring and processing blood pressure.

It is still specific subject matter of this invention a computer-readable memory medium, having a program stored therein, characterised in that the program is the computer program just described.

The method according to the invention uses and processes the signal of blood pressure of a patient for determining the set of the characteristics of the patient's physiopathological system and of the characteristics of the external detecting system so as to evaluate the right interaction between such two systems, thus determining the right underdamping.

More in particular, the method according to the invention is substantially based on a dynamic low-pass filter applied on a detected pressure signal (e.g. from radial, femoral, aorta, or pulmonary artery), wherein the filter, directly working in the time domain, also takes account of the coupling between pressure line and characteristic dynamic impedance, obtained instant by instant from the analysis of the pressure signal (or curve) so as to determine the most adequate operating frequency for the used pressure line. In other words, the method according to the invention is based on a characteristic set of conditions on the values of several parameters of the pressure signal, linked to the result of the coupling of the characteristic dynamic impedance of the cardiocirculatory system to the pressure detecting system, instead of a characteristic frequency spectrum. In this regard, the detected pressure signal to which the method according to the invention is applied may be also a recorded signal that is subsequently analysed by subjecting the same to the method according to the invention, the scope of protection of which does not hence comprise any invasive surgical step on the patient's body.

The method according to the invention allows to determine the adequate impedance related to the heart-circle energy for correcting and determining the true pressure and hence, from the relationship P-V (Pressure-Volume), for determining the correct blood flow linked to the re-corrected pressure waveform and/or for determining the cardiac contractility due to the resulting correct pressure wave. Such corrections for obtaining the adequate pressure are valid for both filling and optical fibre detecting systems, as well as for non-invasive piezo-oscillometric detectors (all always working on the coupling between the impedance of the detecting system and the impedance of the cardiocirculatory system). Also, such corrections for pressure signals detected in both central and peripheral arterial system, such as for instance in pulmonary artery, in aorta, in femoral artery, and in radial artery.

The advantages offered by the method according to the invention are numerous.

First of all, by measuring the coupling between measuring line and patient's cardiocirculatory system, it allows to solve the problems of coupling of the arterial pressure lines to the dynamic characteristics of the patient of whom the arterial pressure, often variable from beat to beat, is measured.

Moreover, by applying a correct dynamic damping, the method according to the invention allows the elimination of any artefact from the detected pressure signal, obtaining a correct measurement of the arterial pressure and dynamic impedance, making possible to go back from the peripheral pressure to the estimation of the maximum derivative of the pressure within the left ventricle ($[dP/dt]_{max}$) that has generated the pulse detected at the periphery. In fact, also in the basis of the maximum derivative of the peripheral pressure the method according to the invention determines a correction factor (i.e. a low-pass filter) that is applied to such peripheral pressure for estimating pressure at the ventricle, taking account of the coupling between measurement line and patient's cardiocirculatory system (whereby, for instance, in case of rigid peripheral vessel, it is necessary to apply a high correction). This entails that, through the filtering dynamically applied by the method according to the invention, the contribution related to arterial vessel rigidity is removed, leaving the basic component related to the characteristics of the ventricle that has generated the pressure pulse.

In other words, besides the measurement of the arterial pressure, the method according to the invention allows to determine a correction factor that estimates the maximum derivative $dP/dt_{max}$ of the ventricle pressure, estimating an energy efficiency of the whole cardiocirculatory system, providing an estimate of the entropy of the biological system; in fact, through the concept of efficiency it is possible to take account of the "irrecoverable" mechanical energy present during a cardiac cycle. Such efficiency describes how much is consumed from the "reserves" of the biological system of the body under consideration, since reserve consumption means consuming "the components" of the physiological system (e.g.: organs, glands (bio-chemical reactions), cardiac electrical system, etc.).

BRIEF DESCRIPTION OF THE DRAWINGS

The present invention will be now described, by way of illustration and not by way of limitation, according to its preferred embodiments, by particularly referring to the Figures of the enclosed drawings, in which.

DETAILED DESCRIPTION

The inventor has developed a method for measuring the blood pressure, starting from a detected pressure signal, that operates in the time domain for discriminating whether the detected signal is an adequate measurement or not and, where it is not, the analysis in the time domain automatically selects a low-pass filter to apply for having correct blood pressure values and wave form. In this regard, the inventor has verified that the method according to the invention provides a pressure signal having an adequate underdamping through tests made with the square wave test before and after application of the filter by the method according to the invention.

Preferably, the detected pressure signal is made available through invasive detecting technique, e.g. a filling pressure line or optical fibres technique in femoral, radial, brachial, aorta, or pulmonary artery, or through non invasive detecting technique, e.g. both piezoelectric and oscillometric plethysmography. However, the detected pressure signal to which the method according to the invention is applied may be also a recorded signal subsequently analysed by subjecting it to the method according to the invention, the scope of protection of which hence does not comprise any invasive surgical step on the patient's body.

More in particular, the method according to the invention is based on the pulsatile frequency (i.e. it uses the whole time range of the heart beat and the relative distances of the individual pressure points within the same beat), some characteristic points of the heart beat determined through the first derivative of the detected arterial pressure (dP/dt) and the second derivative of the detected pressure ($d^2P/dt^2$), and some values of dynamic impedance $Z_d(t)$ in specific instants of the direct wave of pressure (propagating from heart to periphery) and of the reflected waves of pressure (propagating from periphery to heart).

Starting from the thus obtained values of dynamic impedance, the method checks whether the pressure signal constitutes an adequate measurement, and where it does not the method selects the cutoff frequency, preferably ranging from 0.5 Hz to 100 Hz, more preferably from 2 Hz to 80 Hz, still more preferably from 3 Hz to 60 Hz, of the low-pass filter to apply to the detected pressure signal, so that it is the most adequate one to the detection instant conditions, so that the method dynamically adapts to the detection variations which may also occur from beat to beat and from instant to instant.

In other words, the method according to the invention exploits the peculiar characteristics of the pulsatile beat under consideration, and through them it determines a low-pass filter with variable cutoff frequency in order to apply an adequate underdamping.

Figure 1A:
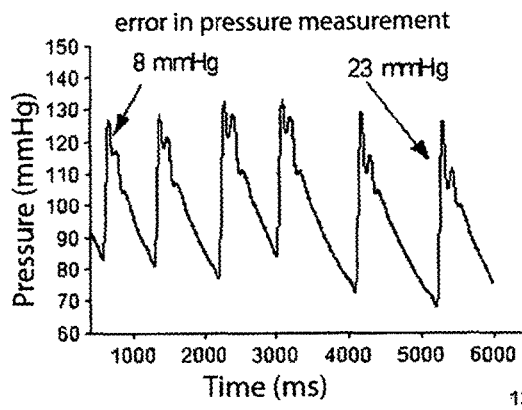
FIG. 1 shows a blood pressure signal (FIG. 1a) and the different result that a conventional system for measuring arterial pressure obtains on a specific beat by applying none or three different cutoff frequencies (see FIG. 1b)
Figure 1B:
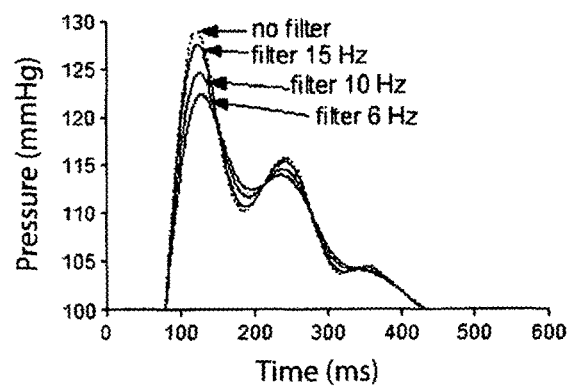
Figure 2A:
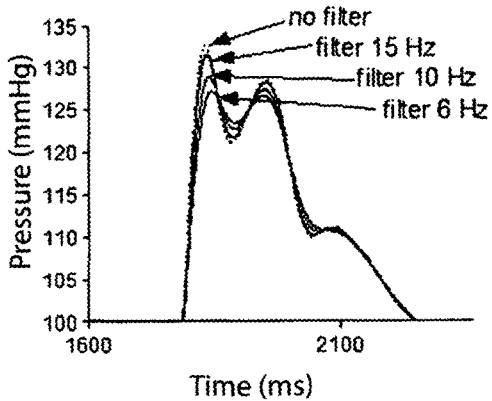
FIG. 2 shows two consecutive beats in the same blood pressure signal obtained by applying with a conventional system none or three different cutoff frequencies.
Figure 2B:
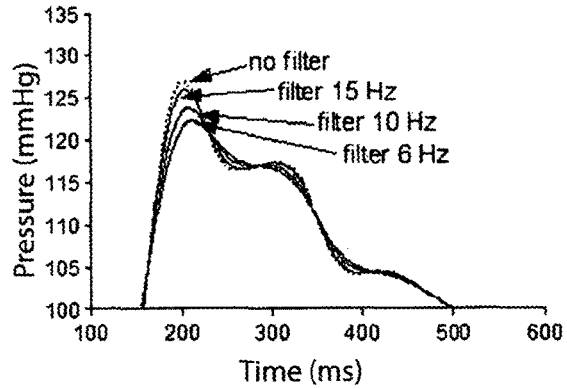
Figure 3A:
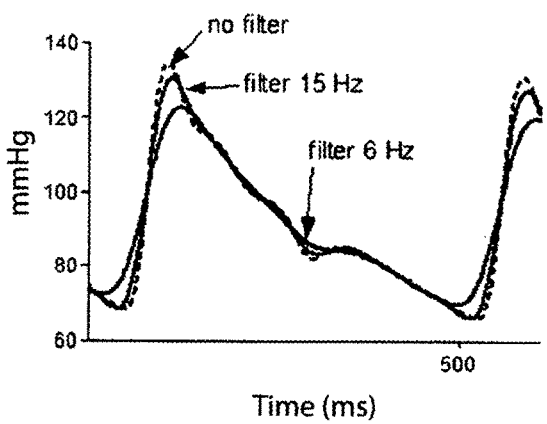
FIG. 3 shows a beat obtained by applying with a conventional system none or two different first cutoff frequencies (FIG. 3a) and by applying with a conventional system none or a second cutoff frequency (FIG. 3b)
Figure 3B:
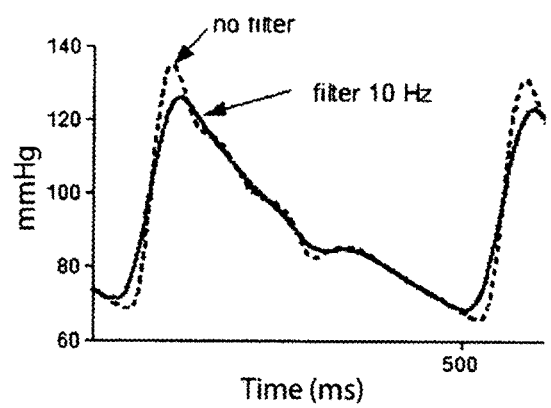
Figure 4A:
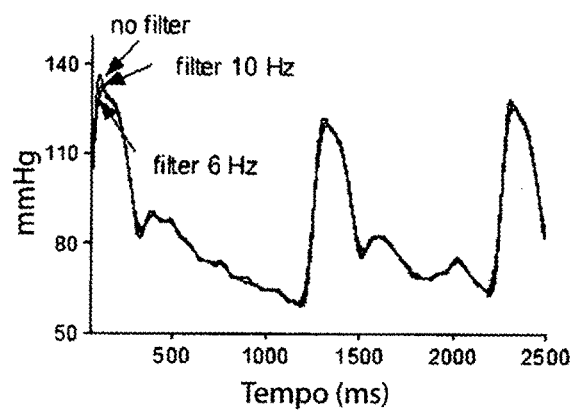
FIG. 4 shows two blood pressure signals obtained by applying with a conventional system none or two identical filters.
Figure 4B:
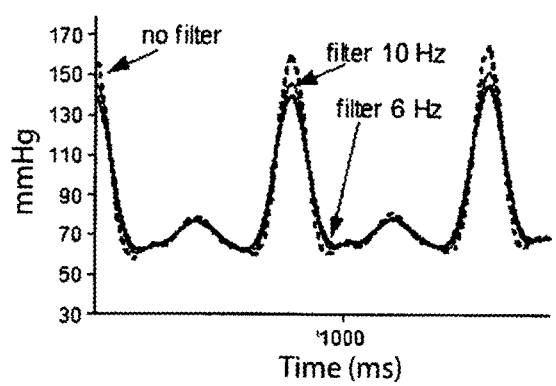
Figure 5:
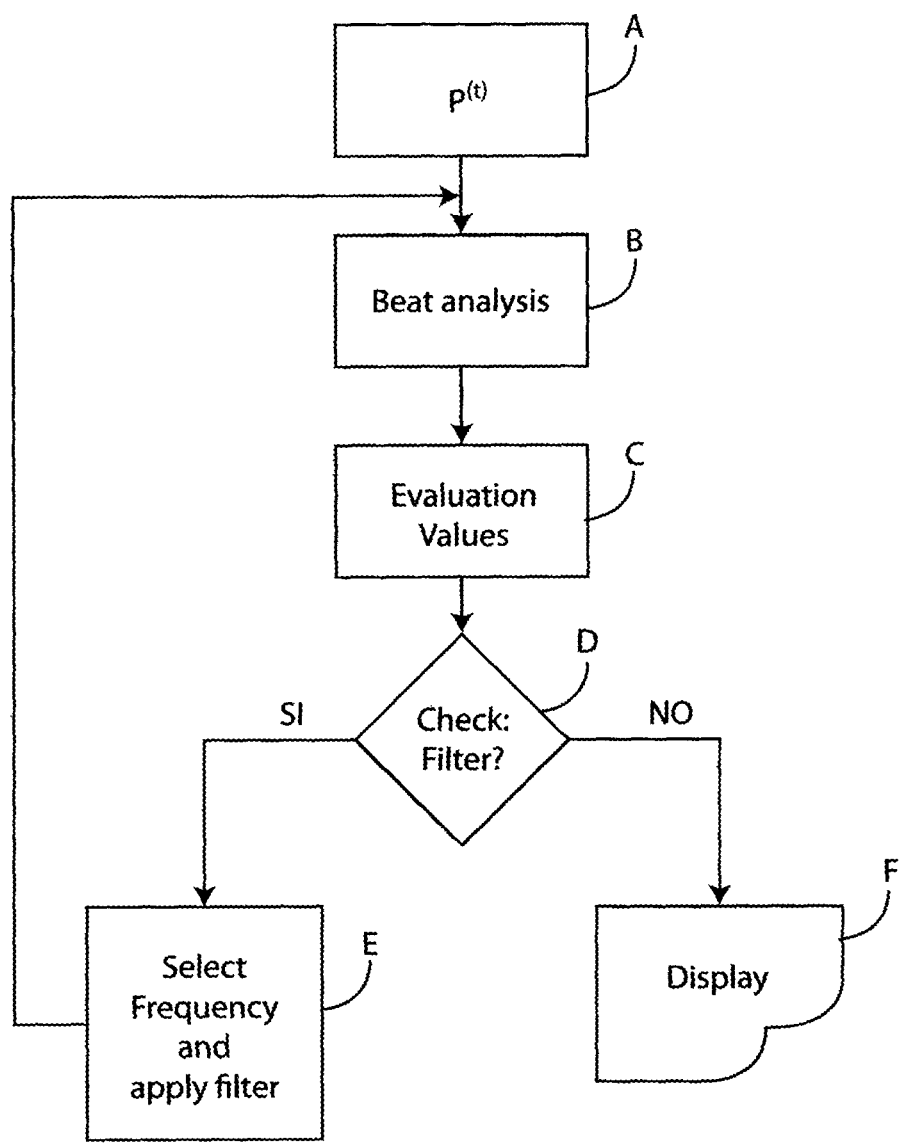
FIG. 5 shows a block diagram of a preferred embodiment of the automatic method according to the invention.

With reference to FIG. 5, it may be observed that the preferred embodiment of the method according to the invention comprises the following steps:

A. having a pressure signal detected through pressure transducer (preferably through invasive arterial pressure line or through non invasive technique, e.g. through plethysmographic oscillometric method), that is sampled, preferably with sampling frequency equal to 1000 Hz;

B. automatically analysing and discriminating the morphology of the sampled pressure wave (i.e. the signal) for each heart beat (going from an initial diastolic pressure point to the subsequent diastolic pressure point, considering as point of diastolic pressure of the beat the initial point of the beat, i.e. the initial diastolic pressure point);

C. for each heart beat, determining some evaluation values consisting in (or comprising) an impedance of the direct wave of pressure and an impedance of the reflected waves of pressure and a consequent energy efficiency of the whole cardiocirculatory system;

D. checking whether it is necessary to apply a low-pass filter and, in the case where the check has positive outcome, making step E, otherwise making step F assuming that the measured pressure signal is identical to the sampled pressure signal;

E. selecting the cutoff frequency of the low-pass filter, on the basis of the analysis of step B and of the determination of step C, and applying the low-pass filter to the sampled pressure signal, obtaining a new sampled pressure signal, and returning to step B;

F. outputting the measured pressure signal, preferably displaying the same on a display.

Step B of automatic analysis of the morphology of the pressure wave (i.e. the signal) detected during a heart beat analyses and discriminates the form of an heart beat by detecting both pressure characteristics and time characteristics (which, as it will be shown below, are considered as ranges starting from the instant of beginning of the beat— i.e. the instant of the initial diastolic pressure—or, backward, from the instant of end of the beat) related to specific points starting from the instant of beginning of the beat, in particular the characteristic points of diastolic pressure (that is initial in the beat), of systolic pressure, of dicrotic point, and of resonance in the individual heart beat.

In greater detail, step B comprises the following substeps:

B.1 determining the pressure and instant of the diastolic pressure point (corresponding to the "initial" absolute minimum of the pressure signal in the individual heart beat), of the systolic pressure point (corresponding to the absolute maximum of the pressure signal in the individual heart beat), and of the dicrotic point (corresponding to the point in which the heart aortic valve closes and that mathematically corresponds to a point of local maximum of the second derivative or of local minimum of the pressure curve occurring immediately after the systolic pressure point), B.2 determining the total number $N_{dP\_max}$ of local maximum points (including the absolute maximum) of the first derivative dP/dt of the (sampled) pressure signal in the range of the individual heart beat;

B.3 determining the local maximum points (including the absolute maximum) of the second derivative $d^2P/dt^2$ of the (sampled) pressure signal in the range of the individual heart beat; and B.4 selecting the $N_{dP\_max}$ local maximum points of the second derivative $d^2P/dt^2$ having largest values (i.e. selecting a number of local maximum points of the second derivative $d^2P/dt^2$ equal to the total number $N_{dP\_max}$ of local maximum points of the first derivative dP/dt as previously determined) and determining the related $N_{dP\_max}$ time instants $t_{d2P\_max}(i)$ (with i ranging from 1 to $N_{dP\_max}$) in which they occur, assuming the pressure signal points in such $N_{dP\_max}$ instants $t_{d2P\_max}(i)$ as resonance points.

In particular, the link between number of local maxima of the second derivative $d^2P/dt^2$ and total number $N_{dP\_max}$ of local maximum points of the first derivative dP/dt in the range of the individual heart beat allows to eliminate the local maximum points of the second derivative $d^2P/dt^2$ due to noise. In this regard, the diastolic peak point (i.e. the point of highest local maximum after the dicrotic point and after the possible hump after the dicrotic point) is always selected in step B.4 among the resonance points.

By way of example and not by way of limitation, the heart beat and the related characteristic pressure points may be discriminated and determined through an automatic method for discriminating the heart beat similar to that described in Application WO 2004/084088.

Figure 6:
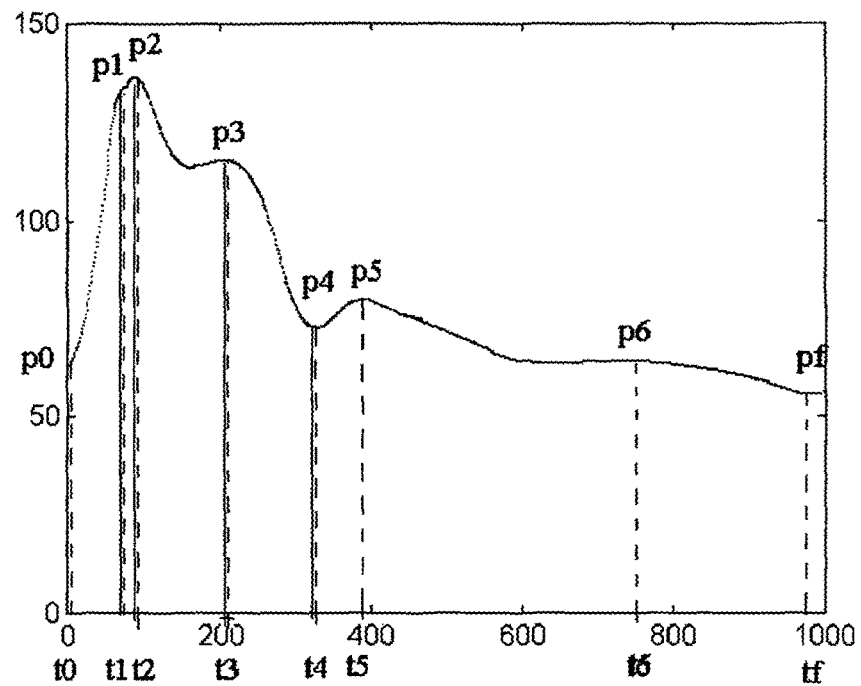
FIG. 6 shows a pressure signal of an individual heart beat to which the method of FIG. 5 is applied.

By way of example and not by way of limitation, FIG. 6 shows the pressure signal of an individual heart beat wherein:

p0 is the value of diastolic pressure (that is initial in the beat), at the instant t0 of beginning of the beat (i.e. instant of the initial diastolic pressure point of the beat);

p2 is the systolic pressure value, at the instant t2 of the systolic pressure point;

p4 is the pressure value at the dicrotic point, occurring at the instant t4;

p1, p3, p5, p6, and pf are the values of pressure at the resonance points occurring at the instants t1, t3, t5, t6 and tf (determined on the basis of the total number $N_{dP\_max}$ of local maximum points of the first derivative dP/dt, equal to 5, and of the selection of corresponding 5 points—having largest values—of local maxima of the second derivative $d^2P/dt^2$).

In FIG. 6, point p5 is the hump following the dicrotic point, while the point p6 is the diastolic peak (i.e. the local maximum following the dicrotic point and the possible hump immediately subsequent to the latter).

Step C determines an evaluation value of an energy efficiency of the whole cardiocirculatory system, providing an estimate of the entropy of the biological system. In particular, such energy efficiency is determined as a quantity that in the following is defined as Result of the Energy ratio of the System, or RES, of the cardiocirculatory system obtained on the basis of the impedance of the direct wave of pressure and of the reflected waves of pressure obtained from the morphology of the pressure signal in a heart beat. Such impedances are determined by considering pressures and related time instants of the characteristic points of the heart beat, which comprise not only the points of diastolic pressure (that is initial in the beat), of systolic pressure, and of dicrotic point (which are placed in the time range comprising the diastole-systole and systole-dicrotic point sub-ranges—i.e. in the systolic phase of the individual heart beat), but also the resonance points determined during a heart beat in step B (namely in sub-step B.4) described above, among which resonance points the point of diastolic peak (i.e. peak after the dicrotic point in the diastolic phase of the individual heart beat) is always present.

In greater detail step C comprises the following sub-steps:

C.1 determining the impedance $Z_D$ of the direct wave of pressure on the basis of a sum of dynamic impedances of a first series of points of the heart beat (series_1) comprising those points among the aforementioned characteristic ones which belong to the systolic phase of the individual heart beat (i.e. in the range from the initial diastolic pressure point up to the dicrotic point), except the initial diastolic point;

C.2 the impedance $Z_R$ of the reflected waves of pressure is determined on the basis of a sum of dynamic impedances of a second series of points of the heart beat (series_2) comprising all the aforementioned characteristic points (which belongs to the whole heart beat);

C.3 determining the RES value as ratio between the impedance $Z_D$ of the direct wave and the impedance $Z_R$ of the reflected waves.

In particular, in relation to the impedance $Z_D$ of the direct wave of pressure, for each point of the first series a respective direct dynamic impedance $Z_{d\_D}(t)$ is determined, given by the ratio between the pressure value at that point and the distance of the respective time instant from the initial instant of the beat, i.e. from the instant of the initial diastolic point (this is the reason why in the first series the initial diastolic point is not considered, since its dynamic impedance would have value 0 at denominator). The value of the impedance $Z_D$ of the direct wave of pressure is obtained by summing with alternate signs the thus determined dynamic impedances of the points of the first series, ordered according to their time order starting from the instant of the initial diastolic pressure up to the dicrotic point instant, starting to consider with a positive sign the dynamic impedance of the first point of the first series.

Similarly, in relation to the impedance $Z_R$ of the reflected waves of pressure, for each point of the second series a respective reflected dynamic impedance $Z_{d\_R}(t)$ is also determined, given by the ratio between the pressure value at that point and the distance of the respective time instant from the final instant of the beat. The value of the impedance $Z_R$ of the reflected waves of pressure is obtained by summing with alternate signs the thus determined dynamic impedances of the points of the second series, ordered according to their reverse time order starting from the final instant of the beat down to the instant of the initial diastolic pressure, starting to consider with a positive sign the dynamic impedance of the first point of the second series.

In other words, the impedances $Z_D$ of the direct wave and $Z_R$ of the reflected waves of pressure are each given by a respective series of terms (i.e. the respective direct and reflected dynamic impedances $Z_{d\_D}(t)$ and $Z_{d\_R}(t)$) which are oscillating (since they are considered with alternate signs) the value of which progressively becomes smaller and smaller (since the value at denominator of the dynamic impedances progressively increases).

As said, the RES value is determined as ratio between the impedance $Z_D$ of the direct wave of pressure (determined on the basis of the first series of points) and the impedance $Z_R$ of the reflected waves of pressure (determined on the basis of the second series of points):

$$RES = Z_D/Z_R$$

Such value of RES represents an energy efficiency for obtaining a given homeostasis of the whole cycle of the cardiocirculatory-respiratory system.

In the example (and not limiting) graph of FIG. 6, the points belonging to the first series (series_1) are indicated with continuous vertical lines (from the time axis up to the pressure value at the related point) and the points belonging to the second series (series_2) are indicated with dotted vertical lines, whereby the points belonging to both the first and the second series are indicated with a pair of vertical lines (one continuous and the other dotted). As shown, the first series comprises (in the time order starting from the instant of the initial diastolic pressure up to the dicrotic point instant) the points indicated with p1, p2, p3, and p4, while the second series comprises (in the reverse time order starting from the final instant of the beat down to the instant of the initial diastolic pressure) the points indicated with pf, p6, p5, p4, p3, p2, p1, p0.

The value of the impedance $Z_D$ of the direct wave of pressure, for the beat shown in FIG. 6, is equal to $$Z_D = \frac{p1}{t1} - \frac{p2}{t2} + \frac{p3}{t3} - \frac{p4}{t4}$$

while the value of the impedance $Z_R$ of the reflected waves of pressure is equal, by assuming that the period of the individual heart beat shown in Figure is T, to $$Z_R = \frac{pf}{(T-tf)} - \frac{p6}{(T-t6)} + \frac{p5}{(T-t5)} - \frac{p4}{(T-t4)} + \frac{p3}{(T-t3)} - \frac{p2}{(T-t2)} + \frac{p1}{(T-t1)} - \frac{p0}{(T-t0)}$$

Checking step D uses, as said, a characteristic set of conditions on the quantities obtained in steps B and C for determining whether the individual heart beat is affected by underdamping, i.e. whether the systolic pressure is over-estimated and the diastolic pressure is under-estimated or whether, on the contrary, the morphology of the heart beat is correct. If such evaluation detects that the heart beat is within the limits imposed by such characteristic set of conditions, then the method does not apply any frequency filter and gives (in step F) a measured pressure signal equal to the sampled pressure signal that is unchanged in its frequencies and amplitudes. Instead, if the characteristics of the heart beat under examination are within ranges defined by such characteristic set of conditions, step E corrects the sampled pressure signal by changing its spectrum by applying a low-pass filter of which it determines the cutoff frequency, and step B for analysing the sampled pressure signal thus obtained from filtering and step C for determining evaluation values are executed again, checking in a new step D whether the values of the obtained quantities are within the limits imposed by such characteristic set of conditions or not. In other words, the sampled pressure signal of the heart beat that is filtered once is analysed again: if the values of the obtained quantities are in accordance with the ranges defined by such characteristic set of conditions, then the method gives (in step F) a measured pressure signal equal to the sampled pressure signal obtained from the last filtering (without applying any further filtering); instead, if the values of the obtained quantities are not within the limits imposes by such characteristic set of conditions, then filtering is repeated, with a suitably selected cutoff frequency, and the method is iteratively executed again from step B until a signal is obtained the obtained quantities of which are in accordance with the ranges defined by such characteristic set of conditions.

In greater detail, step D checks whether, for the RES value determined in step C, the values of the first derivative dP/dt of the pressure signal and the values of the second derivative $d^2P/dt^2$ of the pressure signal in the whole beat under consideration are lower than respective values $T_d$ and $T_{d2}$ of maximum threshold (functions of the RES value), and in such case it is not necessary to apply any filter to the pressure signal and the method passes to directly execute step F, otherwise the method passes to directly execute step E, by applying a low-pass filter to the pressure signal of which it determines the cutoff frequency, and returns to execute the steps starting from step B.

In particular, the possible values of RES are subdivided into three or more, preferably four, adjacent ranges of variability, and the values $T_d$ and $T_{d2}$ depend on the range to which the RES value determined in step C belongs. Preferably:

if the value of RES is not lower (or even larger) than a minimum threshold $T_{RES\_min}$ not lower than 0.3, preferably not lower than 0.4, more preferably not lower than 0.5, the value $T_d$ of maximum threshold of the first derivative dP/dt of the pressure signal is not larger than 1.2 mmH/ms, preferably not larger than 1.1 mmH/ms, more preferably not larger than 1.0 mmH/ms, and the value $T_{d2}$ of maximum threshold of the second derivative $d^2P/dt^2$ of the pressure signal is not larger than 0.2 mmH/ms$^2$, preferably not larger than 0.17 mmH/ms$^2$, more preferably not larger than 0.15 mmH/ms$^2$, if the value of RES is variable within a first (mathematically open or closed) range the lower endpoint of which is larger than 0 and the upper endpoint of which is not larger than the minimum threshold $T_{RES\_min}$, the first range preferably varying from 0.3 a 0.5, the value $T_d$ of maximum threshold of the first derivative dP/dt of the pressure signal is not larger than 1.6 mmH/ms, preferably not larger than 1.4 mmH/ms, more preferably not larger than 1.2 mmH/ms, and the value $T_{d2}$ of maximum threshold of the second derivative $d^2P/dt^2$ of the pressure signal is not larger than 0.25 mmH/ms$^2$, preferably not larger than 0.22 mmH/ms$^2$, more preferably not larger than 0.20 mmH/ms$^2$, if the value of RES is variable within a second range (mathematically open or closed) contiguous to and preceding the first range (in the sense that the lower endpoint of the first range coincides with the upper endpoint of the second range), the lower endpoint of which is not lower than 0, preferably equal to 0, the value $T_d$ of maximum threshold of the first derivative dP/dt of the pressure signal is not larger than 1.6 mmH/ms, preferably not larger than 1.4 mmH/ms, more preferably not larger than 1.2 mmH/ms, and the value $T_{d2}$ of maximum threshold of the second derivative $d^2P/dt^2$ of the pressure signal is not larger than 0.35 mmH/ms$^2$, preferably not larger than 0.30 mmH/ms², more preferably not larger than 0.27 mmH/ms², still more preferably not larger than 0.25 mmH/ms², if the value of RES is lower (or even not larger) than a maximum threshold $T_{RES\_max}$ coinciding with the lower endpoint of the second range, the value $T_d$ of maximum threshold of the first derivative dP/dt of the pressure signal is not larger than 2.0 mmH/ms, preferably not larger than 1.8 mmH/ms, more preferably not larger than 1.6 mmH/ms, and the value $T_{d2}$ of maximum threshold of the second derivative d²P/dt² of the pressure signal is not larger than 0.45 mmH/ms², preferably not larger than 0.40 mmH/ms², more preferably not larger than 0.37 mmH/ms², still more preferably not larger than 0.35 mmH/ms².

In the preferred embodiment of the method according to the invention, checking step D ascertains that it is not necessary to apply any filter to the pressure signal when any one of the following four sets of conditions is met:

RES≥0.5, the first derivative dP/dt is lower than 1.0 mmH/ms in the whole heart beat, and the second derivative d²P/dt² is lower than 0.15 mmH/ms² in the whole heart beat;

0.3≤RES<0.5, the first derivative dP/dt is lower than 1.2 mmH/ms in the whole heart beat, and the second derivative d²P/dt² is lower than 0.2 mmH/ms² in the whole heart beat;

0.0≤RES<0.3, the first derivative dP/dt is lower than 1.2 mmH/ms in the whole heart beat, and the second derivative d²P/dt² is lower than 0.25 mmH/ms² in the whole heart beat;

RES<0.0, the first derivative dP/dt is lower than 1.6 mmH/ms in the whole heart beat, and the second derivative d²P/dt² is lower than 0.35 mmH/ms² in the whole heart beat.

As said, step E selects the cutoff frequency of the low-pass filter, on the basis of the analysis of step B and of the determination of step C, and applies the low-pass filter to the sampled pressure signal. In particular, step E selects the cutoff frequency of the low-pass filter on the basis of the value of RES and of the values of the first derivative and of the values of the second derivative of the pressure signal in the whole heart beat, as follows: the values of RES are discriminated in three or more, preferably four, adjacent ranges of variability (preferably corresponding to those used in the check in step D), for each one of them the values of the first derivative dP/dt of the pressure signal are discriminated in three or more, preferably six, adjacent ranges of variability, and for at least one of the ranges of the values of the first derivative dP/dt the values of the second derivative d²P/dt² of the pressure signal are discriminated in three or more, preferably four, non overlapping ranges of variability (adjacent to each other and, where applicable, adjacent to the range of values of the second derivative d²P/dt² for which the method does not applies any low-pass filter), thus selecting a corresponding cutoff frequency of the low-pass filter to apply.

In the preferred embodiment of the method according to the invention, step E discriminates the values of RES in four adjacent ranges of variability (corresponding to those used in the check in step D), for each one of them discriminates the values of the first derivative dP/dt of the pressure signal in six adjacent ranges of variability, and for the first one of the ranges of the values of the first derivative dP/dt discriminates the values of the second derivative d²P/dt² of the pressure signal in four adjacent ranges (subsequent to the range corresponding to the set of conditions for which no low-pass filter is applied). In greater detail, the preferred embodiment determines the cutoff frequency of the filter as follows:

1. if the value of RES meets the condition RES≥0.5
   1.1 if the values of the first derivative in the whole heart beat meet the condition $dP/dt<1.0$ mmH/ms, 1.1.1 if the values of the second derivative in the whole heart beat meet the condition $0.15$ mmH/ms≤$d^2P/dt^2$<$0.25$ mmH/ms a low-pass filter with cutoff frequency equal to 15 Hz is applied;

1.1.2 if the values of the second derivative in the whole heart beat meet the condition $0.25$ mmH/ms≤$d^2P/dt^2$<$0.30$ mmH/ms a low-pass filter with cutoff frequency equal to 12 Hz is applied;

1.1.3 if the values of the second derivative in the whole heart beat meet the condition $0.30$ mmH/ms≤$d^2P/dt^2$<$0.35$ mmH/ms a low-pass filter with cutoff frequency equal to 8 Hz is applied;

1.1.4 if the values of the second derivative in the whole heart beat meet the condition $d^2P/dt^2$≥$0.35$ mmH/ms a low-pass filter with cutoff frequency equal to 7 Hz is applied;

1.2 if the values of the first derivative in the whole heart beat meet the condition $1.0$ mmH/ms≤$dP/dt$<$1.3$ mmH/ms, a low-pass filter with cutoff frequency equal to 12 Hz is applied;

1.3 if the values of the first derivative in the whole heart beat meet the condition $1.3$ mmH/ms≤$dP/dt$<$1.5$ mmH/ms, a low-pass filter with cutoff frequency equal to 8 Hz is applied;

1.4 if the values of the first derivative in the whole heart beat meet the condition $1.5$ mmH/ms≤$dP/dt$<$2.5$ mmH/ms, a low-pass filter with cutoff frequency equal to 7 Hz is applied;

1.5 if the values of the first derivative in the whole heart beat meet the condition $2.5$ mmH/ms≤$dP/dt$<$3.0$ mmH/ms, a low-pass filter with cutoff frequency equal to 6 Hz is applied;

1.6 if the values of the first derivative in the whole heart beat meet the condition $dP/dt$≥$3.0$ mmH/ms, a low-pass filter with cutoff frequency equal to 3 Hz is applied;

2. if the value of RES meets the condition 0.3≤RES<0.5
   2.1 if the values of the first derivative in the whole heart beat meet the condition $dP/dt<1.2$ mmH/ms, 2.1.1 if the values of the second derivative in the whole heart beat meet the condition $0.2 \text{ mmH/ms} \leq d^2P/dt^2 < 0.25 \text{ mmH/ms}$ a low-pass filter with cutoff frequency equal to 15 Hz is applied;

2.1.2 if the values of the second derivative in the whole heart beat meet the condition $0.25 \text{ mmH/ms} \leq d^2P/dt^2 < 0.35 \text{ mmH/ms}$ a low-pass filter with cutoff frequency equal to 12 Hz is applied;

2.1.3 if the values of the second derivative in the whole heart beat meet the condition $0.35 \text{ mmH/ms} \leq d^2P/dt^2 < 0.45 \text{ mmH/ms}$ a low-pass filter with cutoff frequency equal to 8 Hz is applied;

2.1.4 if the values of the second derivative in the whole heart beat meet the condition $d^2P/dt^2 \geq 0.45 \text{ mmH/ms}$ a low-pass filter with cutoff frequency equal to 7 Hz is applied;

2.2 if the values of the first derivative in the whole heart beat meet the condition $1.2 \text{ mmH/ms} \leq dP/dt < 1.5 \text{ mmH/ms}$, a low-pass filter with cutoff frequency equal to 13 Hz is applied;

2.3 if the values of the first derivative in the whole heart beat meet the condition $1.5 \text{ mmH/ms} \leq dP/dt < 1.8 \text{ mmH/ms}$, a low-pass filter with cutoff frequency equal to 10 Hz is applied;

2.4 if the values of the first derivative in the whole heart beat meet the condition $1.8 \text{ mmH/ms} \leq dP/dt < 2.5 \text{ mmH/ms}$, a low-pass filter with cutoff frequency equal to 8 Hz is applied;

2.5 if the values of the first derivative in the whole heart beat meet the condition $2.5 \text{ mmH/ms} \leq dP/dt < 3.5 \text{ mmH/ms}$, a low-pass filter with cutoff frequency equal to 6 Hz is applied;

2.6 if the values of the first derivative in the whole heart beat meet the condition $dP/dt \geq 3.5 \text{ mmH/ms}$, a low-pass filter with cutoff frequency equal to 3 Hz is applied;

3. if the value of RES meets the condition $0.0 \leq \text{RES} < 0.3$ 3.1 if the values of the first derivative in the whole heart beat meet the condition $dP/dt < 1.2 \text{ mmH/ms}$, 3.1.1 if the values of the second derivative in the whole heart beat meet the condition $0.25 \text{ mmH/ms} \leq d^2P/dt^2 < 0.30 \text{ mmH/ms}$ a low-pass filter with cutoff frequency equal to 15 Hz is applied;

3.1.2 if the values of the second derivative in the whole heart beat meet the condition $0.30 \text{ mmH/ms} \leq d^2P/dt^2 < 0.40 \text{ mmH/ms}$ a low-pass filter with cutoff frequency equal to 12 Hz is applied;

3.1.3 if the values of the second derivative in the whole heart beat meet the condition $0.40 \text{ mmH/ms} \leq d^2P/dt^2 < 0.50 \text{ mmH/ms}$ a low-pass filter with cutoff frequency equal to 8 Hz is applied;

3.1.4 if the values of the second derivative in the whole heart beat meet the condition $d^2P/dt^2 \geq 0.50 \text{ mmH/ms}$ a low-pass filter with cutoff frequency equal to 5 Hz is applied;

3.2 if the values of the first derivative in the whole heart beat meet the condition $1.2 \text{ mmH/ms} \leq dP/dt < 1.5 \text{ mmH/ms}$, a low-pass filter with cutoff frequency equal to 13 Hz is applied;

3.3 if the values of the first derivative in the whole heart beat meet the condition $1.5 \text{ mmH/ms} \leq dP/dt < 1.8 \text{ mmH/ms}$, a low-pass filter with cutoff frequency equal to 10 Hz is applied;

3.4 if the values of the first derivative in the whole heart beat meet the condition $1.8 \text{ mmH/ms} \leq dP/dt < 2.5 \text{ mmH/ms}$, a low-pass filter with cutoff frequency equal to 8 Hz is applied;

3.5 if the values of the first derivative in the whole heart beat meet the condition $2.5 \text{ mmH/ms} \leq dP/dt < 3.5 \text{ mmH/ms}$, a low-pass filter with cutoff frequency equal to 6 Hz is applied;

3.6 if the values of the first derivative in the whole heart beat meet the condition $dP/dt \geq 3.5 \text{ mmH/ms}$, a low-pass filter with cutoff frequency equal to 3 Hz is applied;

4. if the value of RES meets the condition $\text{RES} < 0.0$ 4.1 if the values of the first derivative in the whole heart beat meet the condition $dP/dt < 1.6 \text{ mmH/ms}$, 4.1.1 if the values of the second derivative in the whole heart beat meet the condition $0.35 \text{ mmH/ms} \leq d^2P/dt^2 < 0.40 \text{ mmH/ms}$ a low-pass filter with cutoff frequency equal to 15 Hz is applied;

4.1.2 if the values of the second derivative in the whole heart beat meet the condition $0.40 \text{ mmH/ms} \leq d^2P/dt^2 < 0.45 \text{ mmH/ms}$ a low-pass filter with cutoff frequency equal to 12 Hz is applied;

4.1.3 if the values of the second derivative in the whole heart beat meet the condition $0.45 \text{ mmH/ms} \leq d^2P/dt^2 < 0.50 \text{ mmH/ms}$ a low-pass filter with cutoff frequency equal to 11 Hz is applied;

4.1.4 if the values of the second derivative in the whole heart beat meet the condition $d^2P/dt^2 \geq 0.50$ mmH/ms a low-pass filter with cutoff frequency equal to 10 Hz is applied;

4.2 if the values of the first derivative in the whole heart beat meet the condition 1.6 mmH/ms$\leq dP/dt <$1.8 mmH/ms, a low-pass filter with cutoff frequency equal to 13 Hz is applied;

4.3 if the values of the first derivative in the whole heart beat meet the condition 1.8 mmH/ms$\leq dP/dt <$2.0 mmH/ms, a low-pass filter with cutoff frequency equal to 10 Hz is applied;

4.4 if the values of the first derivative in the whole heart beat meet the condition 2.0 mmH/ms$\leq dP/dt <$2.4 mmH/ms, a low-pass filter with cutoff frequency equal to 8 Hz is applied;

4.5 if the values of the first derivative in the whole heart beat meet the condition 2.4 mmH/ms$\leq dP/dt <$3,2 mmH/ms, a low-pass filter with cutoff frequency equal to 6 Hz is applied;

4.6 if the values of the first derivative in the whole heart beat meet the condition $dP/dt \geq 3.2$ mmH/ms, a low-pass filter with cutoff frequency equal to 3 Hz is applied.

The values indicated for the lower and/or upper limits of the various adjacent ranges for the RES, of the various ranges of the first derivative dP/dt and of the various ranges of the second derivative $d^2P/dt^2$, as well as the values indicated for the selected cutoff frequencies, are only indicative and not restrictive, since they can be increased or decreased by an extent preferably not larger than 25%, more preferably not larger than 20%, still more preferably not larger than 15%, even more preferably not larger than 10%.

The inventor has verified through an frequency domain analysis of the frequency spectra of the sampled pressure signal of the heart beat and of its first and second derivates in the frequency domain the effectiveness of the application of the low-pass filter through the method according to the invention.

Finally, step F displays the sampled pressure signal, possibly obtained from the last filtering, on a display, so as to point out the measurement and morphology of the thus obtained pressure signal.

Figure 7:
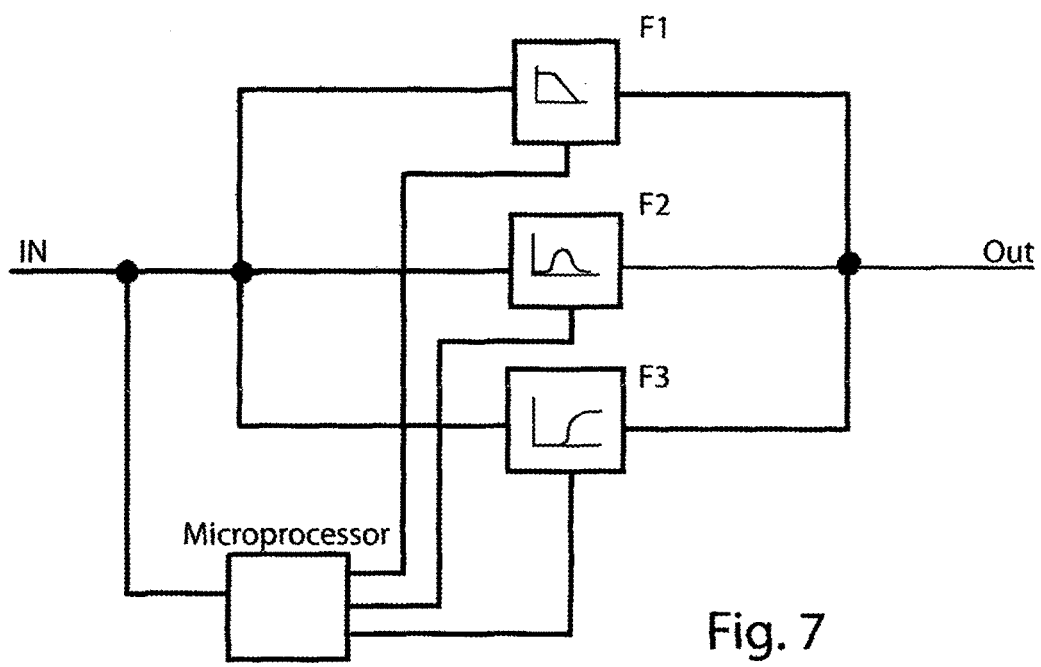
FIG. 7 schematically shows a preferred embodiment of an automatic apparatus according to the invention.

FIG. 7 schematically shows a circuit implementation, that is immediately comprehensible to the skilled in the art, of a preferred embodiment of an automatic apparatus, that executes the method for measuring and processing blood pressure according to the invention. In particular, the circuit stage of FIG. 7 uses one of three possible cutoff frequencies, respectively indicated with F1, F2 and F3; however, it is immediate for those skilled in the art to extend the circuit stage of FIG. 7 to any number of cutoff frequencies. The microprocessor of the stage of FIG. 7 analyses an input pressure signal, present at terminal IN, and determines which one of the three possible cutoff frequencies to apply through an electronic switch controlled by the same microprocessor so as to output, at terminal OUT, the filtered signal; moreover, it is immediate to provide the possibility that the microprocessor can apply again, if necessary, the analysing and selectively filtering steps also to the output signal at the terminal OUT (e.g. through a further electronic switch). It must be understood that the above could be also implemented via software also, through a computer program executing the automatic method for measuring and processing blood pressure according to the invention, without any need for any hardware.

The preferred embodiments have been above described and some modifications of this invention have been suggested, but it should be understood that those skilled in the art can make variations and changes, without so departing from the related scope of protection, as defined by the following claims.

The invention claimed is:

1. An automatic method for measuring and processing blood pressure of a cardiocirculatory system, comprising dynamically analyzing and correcting the pressure measurement by:
   A. one of, invasively or non-invasively, detecting a sampled pressure signal P(t) for one or more heart beats using pressure detectors, each heart beat starting at an initial instant of time coinciding with an initial diastolic pressure point and ending at a final instant of time coinciding with a subsequent diastolic pressure point and comprising a dicrotic point, each beat having a systolic phase going from the initial diastolic pressure point to the dicrotic point; and associating by way of a processor, a processing window to a portion of the sampled pressure signal P(t) corresponding to a heart beat;
   B. automatically analyzing and discriminating morphology of the sampled pressure signal P(t) for the heart beat associated to said processing window by one of, directly in the time domain or from a recorded signal, determining a first derivative dP/dt and a second derivative $d^2P/dt^2$ of the detected sampled pressure signal P(t), and determining an instant of time and pressure value of one or more characteristic points of the sampled pressure signal P(t) selected from the group comprising
   an initial diastolic pressure point,
   a systolic pressure point,
   a dicrotic point, and
   one or more resonance points, each one of which occurs in an instant of time
   wherein a second derivative $d^2P/dt^2$ of the sampled pressure signal P(t) has a local maximum, among which resonance points the point of diastolic peak, defined as the peak after the dicrotic point in the diastolic phase of each heart beat, is always present,
   at least one of the one or more characteristic points of the sampled pressure signal P(t) belonging to the systolic phase of the heart beat associated with the processing window under consideration and being different from the initial diastolic pressure point;
   C. for the heart beat associated with the processing window, determining an energy efficiency defined as a Result of the Energy ratio of the System (RES) through the following:
      C.1 determining a direct dynamic impedance $Z_{d\_D}(t)$ for each one of said one or more characteristic points belonging to the systolic phase of the heart beat associated with the processing window under consideration and different from the initial diastolic pressure point, said direct dynamic impedance $Z_{d\_D}(t)$ being equal to the ratio between a value of the sampled pressure signal P(t) at the characteristic point and interval of time between the respective instant of time and the initial instant of time of the heart beat associated with the processing window under consideration, and determining an impedance $Z_D$ of a direct wave of pressure by summing with alternate signs the values of the direct dynamic impedances $Z_{d\_D}(t)$ ordered according to a first sequence, wherein said first sequence goes from the initial instant of time of the heart beat associated with the processing window under consideration until the instant of time of the dicrotic point, beginning by applying a positive sign to the first direct dynamic impedance $Z_{d\_D}(t)$ in the first sequence;

C.2 determining a reflected dynamic impedance $Z_{d\_R}(t)$ for each one of said one or more characteristic points, said reflected dynamic impedance $Z_{d\_R}(t)$ being equal to the ratio between a value of the sampled pressure signal P(t) at the characteristic point and the interval of time between the respective instant of time of that characteristic point, and the final instant of time of the heart beat associated with the processing window under consideration, and determining an impedance $Z_R$ of reflected waves of pressure by summing with alternate signs the values of the reflected dynamic impedances $Z_{d\_R}(t)$ ordered according to a second sequence, wherein said second sequence goes from the final instant of time of the heart beat associated with the processing window under consideration until the initial instant of time of the heart beat under consideration, beginning by applying a positive sign to the first reflected dynamic impedance $Z_{d\_R}(t)$ in the second sequence; and C.3 determining said energy efficiency RES as a ratio between the impedance $Z_D$ of the direct wave and the impedance $Z_R$ of the reflected waves:

$$RES = Z_D/Z_R$$

D. for said energy efficiency RES determined in step C, checking whether a first derivative dP/dt of the sampled pressure signal P(t) is lower than a first predetermined value $T_d$ of maximum threshold in a whole heart beat associated with the processing window under consideration and whether the second derivative $d^2P/dt^2$ of the sampled pressure signal P(t) is lower than a second predetermined value $T_{d2}$ of maximum threshold in the whole heart beat associated with the processing window under consideration, and in the event that the checking yields at least one of, (1) an outcome that dP/dt of the sampled pressure signal P(t) is not lower than a first predetermined value $T_d$ and (2) an outcome that the second derivative $d^2P/dt^2$ of the sampled pressure signal P(t) is not lower than a second predetermined value $T_{d2}$, performing step E, otherwise, in the case where the checking yields that dP/dt of the sampled pressure signal P(t) is lower than a first predetermined value $T_d$ and the second derivative $d^2P/dt^2$ of the sampled pressure signal P(t) is lower than a second predetermined value $T_{d2}$, performing step F;

E. selecting a cutoff frequency of a low-pass filter on the basis of said energy efficiency RES determined in step C, and also on the basis of the first derivative dP/dt and the second derivative $d^2P/dt^2$ of the sampled pressure signal P(t), and applying said low-pass filter to the sampled pressure signal P(t), thus obtaining a new sampled pressure signal, and returning to execute the preceding steps starting from step B;

F. outputting the sampled pressure signal P(t) on which step B has been performed most recently, and if the sampled pressure signal P(t) comprises one or more heart beats which have not been analyzed yet, shifting the processing window on to the next heart beat of the sampled pressure signal P(t) and returning to execute the preceding steps starting from step B, otherwise making the method come to an end, and wherein steps B to F are executed by the processor.

2. The method according to claim 1, wherein said one or more resonance points are determined in step B through the following sub-steps:

B.1 determining the pressure value and instant of time of the initial diastolic pressure point, of the systolic pressure point, and of the dicrotic point;

B.2 determining a total number $N_{dP\_max}$ of local maximum points of the first derivative dP/dt of the sampled pressure signal P(t) in the heart beat under consideration;

B.3 determining local maximum points of the second derivative $d^2P/dt^2$ of the sampled pressure signal P(t) in the heart beat under consideration; and B.4 selecting a number $N_{dP\_max}$ of local maximum points of the second derivative $d^2P/dt^2$ having largest values, determining $N_{dP\_max}$ time instants $t_{d2P\_max}(i)$ wherein said $N_{dP\_max}$ selected local maximum points of the second derivative $d^2P/dt^2$, occur, and assuming the points of the sampled pressure signal P(t) in such $N_{dPmax}$ time instants $t_{d2P\_max}(i)$ as resonance points.

3. The method according to claim 1, wherein, in step B, said one or more characteristic points of the sampled pressure signal P(t) consist of:
the initial diastolic pressure point,
the systolic pressure point,
the dicrotic point, and
one or more resonance points.

4. The method according to claim 1, wherein the first predetermined value $T_d$ of maximum threshold and the second predetermined value $T_{d2}$ of maximum threshold are functions of said energy efficiency RES determined in step C.

5. The method according to claim 1, wherein step D further comprises checking whether said energy efficiency RES determined in step C belongs to one of three or more adjacent ranges of variability, wherein the first predetermined value $T_d$ of maximum threshold and the second predetermined value $T_{d2}$ of maximum threshold are functions of the range to which said energy efficiency RES determined in step C belongs.

6. The method according to claim 5, wherein, in step E, said cutoff frequency is selected by
defining three or more adjacent ranges of variability of said energy efficiency RES determined in step C and determining in which of said three or more adjacent ranges of variability, said energy efficiency RES determined in step C belongs,
for each one of said three or more adjacent ranges of variability of said energy efficiency RES determined in step C, defining three or more adjacent ranges of variability of the first derivative dP/dt of the sampled pressure signal P(t) in the whole heart beat under consideration and determining in which of said three or more adjacent ranges of variability, the first derivative dP/dt of the sampled pressure signal P(t) in the whole heart beat under consideration belongs, and for each one of said three or more adjacent ranges of variability of the first derivative dP/dt of the sampled pressure signal P(t) in the whole heart beat under consideration, defining three or more non overlapping ranges of variability of the second derivative $d^2P/dt^2$ of the sampled pressure signal P(t) and determining in which of said three or more adjacent ranges of variability the second derivative $d^2P/dt^2$ of the sampled pressure signal P(t) belongs, to which a respective value of said cutoff frequency corresponds.

7. The method according to claim 6, wherein, in step E, the three or more adjacent ranges of variability to which the belonging of said energy efficiency RES determined in step C is discriminated are four adjacent ranges of variability.

8. The method according to claim 6, wherein, in step E, the three or more adjacent ranges of variability to which the belonging of the first derivative dP/dt of the sampled pressure signal P(t) in the whole heart beat under consideration is discriminated are six adjacent ranges of variability.

9. The method according to claim 6, wherein, in step E, the three or more non overlapping ranges of variability to which the belonging of the second derivative $d^2P/dt^2$ of the pressure signal P(t) is discriminated are four non overlapping ranges of variability.

10. The method according to claim 1, wherein said cutoff frequency, in step E, is a constant value decreasing upon increasing the first derivative dP/dt of the sampled pressure signal P(t), under identical values of said energy efficiency RES and of the second derivative $d^2P/dt^2$ of the sampled pressure signal P(t).

11. The method according to claim 1, wherein said cutoff frequency, in step E, is a constant value decreasing upon increasing the second derivative $d^2P/dt^2$ of the sampled pressure signal P(t), under identical values of said energy efficiency RES and of the first derivative dP/dt of the sampled pressure signal P(t).

12. The method according to claim 1, wherein said cutoff frequency ranges from 0.5 Hz to 100 Hz.

13. The method according to claim 12, wherein said cutoff frequency ranges from 2 Hz to 80 Hz.

14. The method according to claim 13, wherein said cutoff frequency ranges from 3 Hz to 60 Hz.

15. The method according to claim 1, wherein in step F the sampled pressure signal P(t) is displayed on a display.

16. The method according to claim 1, wherein step D further comprises checking whether said energy efficiency RES determined in step C belongs to one of four adjacent ranges of variability, wherein the first predetermined value Td of maximum threshold and the second predetermined value $T_{d2}$ of maximum threshold are functions of the range to which said energy efficiency RES determined in step C belongs.

17. An apparatus for automatically measuring and processing blood pressure of a cardiocirculatory system, comprising pressure detectors and a non-transitory computer readable medium having computer executable instructions stored thereon, wherein the instructions include dynamically analyzing and correcting a blood pressure measurement by a method comprising:

A. one of, invasively or non-invasively, detecting a sampled pressure signal P(t) for one or more heart beats using said pressure detectors, each heart beat starting at an initial instant of time coinciding with an initial diastolic pressure point and ending at a final instant of time coinciding with a subsequent diastolic pressure point and comprising a dicrotic point, each beat having a systolic phase going from the initial diastolic point to the dicrotic point, and associating by way of a processor, a processing window to a portion of the sampled pressure signal P(t) corresponding to a heart beat;

B. automatically analyzing and discriminating morphology of the pressure signal P(t) sampled for the heart beat associated with the processing window by one of, directly in the time domain, or from a recorded signal, determining a first derivative dP/dt and a second derivative $d^2P/dt^2$ of the pressure signal P(t), and determining an instant of time and pressure value of one or more characteristic points of the pressure signal P(t) selected from the group comprising the initial diastolic pressure point, a systolic pressure point, the dicrotic point, and one or more resonance points, each one of which occurs in an instant of time wherein a second derivative $d^2P/dt^2$ of the pressure signal P(t) has a local maximum, among which resonance points the point of diastolic peak, defined as the peak after the dicrotic point in the diastolic phase of each heart beat, is always present, at least one of the one or more characteristic points of the pressure signal P(t) belonging to the systolic phase of the heart beat associated with the processing window under consideration and being different from the initial diastolic pressure point;

C. for the heart beat associated with the processing window, determining an energy efficiency defined as a Result of the Energy ratio of the System (RES) through the following:

C.1 determining a direct dynamic impedance $Z_{d\_D}(t)$ for each one of said one or more characteristic points belonging to the systolic phase of the heart beat associated with the processing window under consideration and different from the initial diastolic pressure point, said direct dynamic impedance $Z_{d\_D}(t)$ being equal to the ratio between a value of the pressure signal P(t) at the characteristic point and interval of time from the respective initial instant of time of the heart beat associated with the processing window under consideration, and determining an impedance $Z_D$ of a direct wave of pressure by summing with alternate signs the values of the direct dynamic impedances $Z_{d\_D}(t)$ ordered according to a first sequence, wherein said first sequence goes from the initial instant of time of the heart beat associated with the processing window under consideration until the instant of time of the dicrotic point, beginning to apply a positive sign to the direct dynamic impedance $Z_{d\_D}(t)$ that is the first one in the first sequence;

C.2 determining a reflected dynamic impedance $Z_{d\_R}(t)$ for each one of said one or more characteristic points, said reflected dynamic impedance $Z_{d\_R}(t)$ being equal to the ratio between a value of the pressure signal P(t) at the characteristic point and the interval of time between the respective instant of time of that characteristic point and the final instant of time of the heart beat associated with the processing window under consideration, and determining an impedance $Z_R$ of reflected waves of pressure by summing with alternate signs the values of the reflected dynamic impedances $Z_{d\_R}(t)$ ordered according to a second sequence, wherein said second sequence goes from a final instant of time until the initial instant of time of the heart beat associated to said processing window under consideration, beginning to apply a positive sign to the reflected dynamic impedance $Z_{d\_R}(t)$ that is the first one in the second sequence;

C.3 determining said energy efficiency RES as ratio between the impedance $Z_D$ of the direct wave and the impedance $Z_R$ of the reflected waves:

$$RES = Z_D/Z_R$$

D. for said energy efficiency RES determined in step C, checking whether a first derivative dP/dt of the pressure signal P(t) is lower than a first predetermined value $T_d$ of maximum threshold in the whole heart beat associated with the processing window under consideration and whether the second derivative $d^2P/dt^2$ of the pressure signal P(t) is lower than a second predetermined value $T_{d2}$ of maximum threshold in the whole heart beat associated with the processing window under consideration, and in the case where the checking yields at least one of, (1) an outcome that dP/dt of the sampled pressure signal P(t) is not lower than a first predetermined value $T_d$ and (2) an outcome that the second derivative $d^2P/dt^2$ of the sampled pressure signal P(t) is not lower than a second redetermined value $T_{d2}$ performing step E, otherwise, in the case where the checking yields an outcome that dP/dt of the sampled pressure signal P(t) is lower than a first predetermined value $T_d$ and the second derivative $d^2P/dt^2$ of the sampled pressure signal P(t) is lower than a second predetermined value $T_{d2}$, performing step F;

E. selecting a cutoff frequency of a low-pass filter on the basis of said energy efficiency RES determined in step C, and also on the basis of the first derivative dP/dt and the second derivative $d^2P/dt^2$ of the pressure signal P(t), and applying said low-pass filter to the pressure signal P(t), thus obtaining a new sampled pressure signal, and returning to execute the preceding steps starting from step B;

F. outputting the pressure signal P(t) on which step B has been performed most recently, and if said sampled pressure signal P(t) comprises one or more heart beats which have not been analyzed yet, shifting the processing window on the next heart beat of the sampled pressure signal P(t) and returning to execute the preceding steps starting from step B, otherwise making the method come to an end, and wherein steps B to F are executed by the processor.

18. A non-transitory computer-readable memory medium, having a program stored therein, wherein the program is configured to perform, when operating on a microprocessor, the following steps of an automatic method for dynamically measuring and processing blood pressure:

A. detecting, based on pressure detectors, a sampled pressure signal P(t) for one or more heart beats, each heart beat starting at an initial instant of time coinciding with an initial diastolic pressure point and ending at a final instant of time coinciding with a subsequent diastolic pressure point and comprising a dicrotic point, each beat having a systolic phase going from the initial diastolic pressure point to the dicrotic point; and associating by way of a processor, a processing window to a portion of the sampled pressure signal P(t) corresponding to a heart beat;

B. automatically analyzing and discriminating morphology of the sampled pressure signal P(t) for the heart beat associated with the processing window, determining a first derivative dP/dt and a second derivative $d^2P/dt^2$ of the sampled pressure signal P(t), and determining an instant of time and pressure value of one or more characteristic points of the sampled pressure signal P(t) selected from the group comprising
the initial diastolic pressure point,
a systolic pressure point,
the dicrotic point, and
one or more resonance points, each one of which occurs in an instant of time wherein a second derivative $d^2P/dt^2$ of the pressure signal P(t) has a local maximum,
at least one characteristic point of the sampled pressure signal P(t) belonging to the systolic phase of the heart beat associated with the processing window under consideration and being different from the initial diastolic pressure point;

C. for the heart beat associated with the processing window, determining an energy efficiency defined as a Result of the Energy ratio of the System (RES) through the following sub-steps:

C.1 determining a direct dynamic impedance $Z_{d\_D}(t)$ for each one of said one or more characteristic points belonging to the systolic phase of the heart beat associated with the processing window under consideration and different from the initial diastolic pressure point, said direct dynamic impedance $Z_{d\_D}(t)$ being equal to the ratio between a value of the sampled pressure signal P(t) at the characteristic point and interval of time between the respective instant of time and the initial instant of time of the heart beat associated with the processing window under consideration, and determining an impedance $Z_D$ of a direct wave of pressure by summing with alternate signs the values of the direct dynamic impedances $Z_{d\_D}(t)$ ordered according to a first sequence, wherein the first sequence goes from the initial instant of time of the heart beat associated with the processing window under consideration until the instant of time of the dicrotic point, beginning to apply a positive sign to the direct dynamic impedance $Z_{d\_D}(t)$ that is a first one in the first sequence;

C.2 determining a reflected dynamic impedance $Z_{d\_R}(t)$ for each one of said one or more characteristic points, said reflected dynamic impedance $Z_{d\_R}(t)$ being equal to the ratio between a value of the sampled pressure signal P(t) at the characteristic point and the interval of time between the respective instant of time of that characteristic point and the final instant of time of the heart beat associated with the processing window under consideration, and determining an impedance $Z_R$ of reflected waves of pressure by summing with alternate signs the values of the reflected dynamic impedances $Z_{d\_R}(t)$ ordered according to a second sequence,
wherein said second sequence goes from the final instant of time until the initial instant of time of the heart beat associated with the processing window under consideration, beginning to apply a positive sign to the reflected dynamic impedance $Z_{d\_R}(t)$ that is the first one in the second sequence;

C.3 determining said energy efficiency RES as a ratio between the impedance $Z_D$ of the direct wave and the impedance $Z_R$ of the reflected waves:

$$RES = Z_D/Z_R$$

D. for said energy efficiency RES determined in step C, checking whether a first derivative dP/dt of the pressure signal P(t) is lower than a first predetermined value $T_d$ of maximum threshold in the whole heart beat associated with the processing window under consideration and whether the second derivative $d^2P/dt^2$ of the pressure signal P(t) is lower than a second predetermined value $T_{d2}$ of maximum threshold in the whole heart beat associated with the processing window under consideration, and in the case where the checking yields at least one of, (1) an outcome that dP/dt of the sampled pressure signal P(t) is not lower than a first predetermined value $T_d$ and (2) an outcome that the second derivative $d^2P/dt^2$ of the sampled pressure signal P(t) is not lower than a second predetermined value $T_{d2}$ performing step E, otherwise, in the case where the checking yields an outcome that dP/dt of the sampled pressure signal P(t) is lower than a first predetermined value $T_d$ and the second derivative $d^2P/dt^2$ of the sampled pressure signal P(t) is lower than a second predetermined value $T_{d2}$, performing step F;

E. selecting a cutoff frequency of a low-pass filter on the basis of said energy efficiency RES determined in step C, and also on the basis of the first derivative dP/dt and the second derivative $d^2P/dt^2$ of the sampled pressure signal P(t), and applying said low-pass filter to the pressure signal P(t), thus obtaining a new sampled pressure signal, and returning to execute the preceding steps starting from step B;

F. outputting the sampled pressure signal P(t) on which step B has been performed most recently, and if the sampled pressure signal P(t) comprises one or more heart beats which have not been analyzed yet, shifting said processing window on the next heart beat of the sampled pressure signal P(t) and returning to execute the preceding steps starting from step B, otherwise making the method come to an end, wherein steps B to F are executed by the processor.

* * * * *